United States Patent
Urbancic et al.

(10) Patent No.: US 7,271,307 B2
(45) Date of Patent: Sep. 18, 2007

(54) METHOD FOR IMPROVING THE PERFORMANCE OF A DEHYDROGENATION CATALYST

(75) Inventors: Michael A. Urbancic, Louisville, KY (US); Michael W. Balakos, Buckner, KY (US); Robert J. Gartside, Summit, NJ (US); Robert J. Brummer, Wharton, NJ (US)

(73) Assignee: Sud-Chemie Inc., Louisville, KY (US)

( * ) Notice: Subject to any disclaimer, the term of this patent is extended or adjusted under 35 U.S.C. 154(b) by 268 days.

(21) Appl. No.: 10/695,372

(22) Filed: Oct. 28, 2003

(65) Prior Publication Data

US 2004/0087825 A1    May 6, 2004

Related U.S. Application Data

(60) Provisional application No. 60/421,967, filed on Oct. 29, 2002.

(51) Int. Cl.
C07C 5/327 (2006.01)
C07V 5/333 (2006.01)

(52) U.S. Cl. ...................................... 585/659; 585/654

(58) Field of Classification Search ................ 585/654, 585/659
See application file for complete search history.

(56) References Cited

U.S. PATENT DOCUMENTS 2,419,997 A * 5/1947 Houdry ...................... 585/602
4,409,417 A * 10/1983 Herbstman .................. 585/660

FOREIGN PATENT DOCUMENTS

EP          462094 A1 * 12/1991

* cited by examiner

*Primary Examiner*—Glenn Caldarola
*Assistant Examiner*—In Suk Bullock
(74) *Attorney, Agent, or Firm*—Joan L. Simunic

(57) ABSTRACT

The present development relates to a modification of the Houdry process for the dehydrogenation of aliphatic hydrocarbons, whereby the dehydrogenation cycle is extended, or lengthened, and hydrogen gas is added into the reaction. The combination of the extended cycle with the hydrogen introduction results in a surprising stabilization of the production rate in the dehydrogenation process. The hydrogen gas may be introduced through a recycle step. The process of the present development is demonstrated for the dehydrogenation of propane to propylene.

15 Claims, No Drawings

METHOD FOR IMPROVING THE PERFORMANCE OF A DEHYDROGENATION CATALYST

CROSS-REFERENCE TO RELATED APPLICATIONS

The present application is related to U.S. Provisional Application Ser. No. 60/421,967 filed on Oct. 29, 2002 and incorporated herein in its entirety by reference.

BACKGROUND

The present development relates to an improved method for propylene production utilizing a classical dehydrogenation catalyst. Specifically, the method combines hydrogen recycle with an extended dehydrogenation reaction cycle resulting in a surprising stabilization of the production rate in an aliphatic hydrocarbon dehydrogenation process.

Dehydrogenation of aliphatic hydrocarbons to produce their complementary olefins is a well-known process. In the typical "Houdry" process, an aliphatic hydrocarbon, such as propane, is passed through a dehydrogenation catalyst bed where the hydrocarbon is dehydrogenated to its complementary olefin, such as propylene, the olefin is flushed from the bed, the catalyst is regenerated and reduced, and the cycle is repeated. (See, for example, U.S. Pat. No. 2,419,997 and incorporated herein by reference.)

Theoretically, the catalyst should return to its original state following the regeneration stage. In practice, however, when the catalyst has been on-stream for some extended period of time, the catalyst—as is known in the art for aged catalysts—demonstrates some loss in functionality and the propylene yield gradually decreases. Thus, it would be advantageous if a method could be developed that would decrease the rate of loss of functionality of the catalyst, thereby increasing the catalyst lifetime and, that preferably would improve the activity and the selectivity of the catalyst, thereby maintaining yield of the desired olefins.

SUMMARY OF THE INVENTION

The present development relates to a modification of the Houdry process for the dehydrogenation of aliphatic hydrocarbons, whereby the cycle is extended, or lengthened, and hydrogen recycle is added to the feed. The combination of the extended cycle with the hydrogen recycle results in a surprising stabilization of the production rate in the dehydrogenation process. The process of the present development is demonstrated for the dehydrogenation of propane to propylene.

DETAILED DESCRIPTION OF THE PREFERRED EMBODIMENT

The method of the present invention is intended for use in aliphatic hydrocarbon dehydrogenation reactions, specifically for the production of olefins. The method utilizes a classic dehydrogenation catalyst and is based on a known dehydrogenation process. However, the process is modified such that the process cycle is extended and a hydrogen recycle stage is added.

The catalyst used in the present development is a dehydrogenation catalyst sold under the name Catofin® by Süd-Chemie, Inc. The catalyst is loaded into a reactor bed wherein the bed defines a top section, a middle section and a bottom section. An aliphatic hydrocarbon is fed into the catalyst bed as a gas feed at a preselected flow rate and such that the feed initially contacts the top section of the bed and exits after contact with the bottom section. For the purposes of example herein, the aliphatic hydrocarbon is propane and the target product is propylene.

The process generally follows the typical "Houdry" process as described in U.S. Pat. No. 2,419,997. The Houdry process includes a series of stages wherein the catalyst bed is evacuated, reduced with hydrogen and evacuated, then an aliphatic hydrocarbon is introduced and dehydrogenated, then the catalyst bed is steam purged and regenerated, and the cycle is repeated starting with the reduction stage. In the present development, the length of each stage is controlled by a sequencer, and multiple reactors are controlled from the sequencer. As is known in the art, the reactors are designed to function in tandem, such that while a first set of reactors is receiving feed, a second set of reactors is in the regeneration stage, and a third set of reactors may be in another stage, such as evacuation or purge. (As used herein, "set" as applied to reactors can range from a single reactor to a plurality of reactors acting in parallel.) The stages within the individual reactors then cycle through the known Houdry process, with the sequencer controlling all the reactors simultaneously. Thus, a modification in the timing for the reaction in the first set of reactors automatically results in a change in the timing in the other reactors, or, viewed from a different perspective, a change in length of the reaction stage in the first set of reactors results in a change in length of the process stages in the other reactors controlled by the sequencer.

Extended cycles can be created by the introduction of one or more delays added to the sequencer program. The delay can be introduced by a variety of known methods, and may vary in length. In a preferred embodiment, the delay length is limited to minutes or seconds. Because the sequencer controls several reactors simultaneously, a delay at one stage in the first set of reactors will result in a delay at a different stage in the second set of reactors. Further, for consistent performance, when a delay is introduced in one stage for the first set of reactors, a delay must be introduced at the same stage for the second set of reactors. The overall result then is best understood through example: if there are two sets of reactors and the delay is introduced in the reduction stage, the sequencer will be programmed to apply the delay in the reaction stage to each set of reactors. But, because the reactors function in tandem, the delay at the reduction stage for the first set of reactors may be at the dehydrogenation stage in the second set of reactors—thereby increasing the dehydrogenation time in these reactors. When the second set of reactors then experiences the programmed delay at the reduction stage, the first set of reactors will experience a concomitant delay in the dehydrogenation stage by virtue of acting in tandem with the second set of reactors. Thus, a delay programmed into a particular process stage for a particular set of reactors will actually affect each of the reactors participating in the process in real-time. In general, it is observed that when the feed gas is propane, the propane conversion is increased with the introduction of delays in the sequencer program.

Further, there is a noticeable shift in the temperature profile for the catalyst bed that is observed with the extended cycle. During the normal dehydrogenation cycle times, the temperature of the catalyst bed will vary within a defined temperature range in the top section of the bed, $\Delta T_t$, in the middle section of the bed, $\Delta T_m$, and in the bottom section of the bed, $\Delta T_b$. The extended cycles also demonstrate catalyst bed temperature variations, but the temperature ranges in each section are greater than in a normal cycle. That is, if for the extended cycle, the temperature range in the top section of the bed is defined as $\Delta T_{te}$, in the middle section of the bed as $\Delta T_{me}$, and in the bottom section of the bed as $\Delta T_{be}$, then $\Delta T_{te}$ would be greater than $\Delta T_t$, $\Delta T_{me}$ would be greater than $\Delta T_m$, $\Delta T_{be}$ would be greater than $\Delta T_b$. When propane is the feed gas, the relative temperature changes at the middle and bottom of the bed are greater than at the top bed.

The amount of coke produced increases with the extended cycle. The exact causes for this phenomena are not clear but it is possible that the coke formation is directly linked to the shift in the temperature profile—the longer regeneration time allows higher temperatures to progress deeper into the catalyst bed, and the higher temperatures then cause higher coke make. Regardless of the cause, the higher coke make is detrimental to the life of the catalyst and manifests itself in decreased production of the desired product as the catalyst ages. Thus, while the extended cycle improves conversion, the increased coke makes the extended cycle process less attractive.

The addition of hydrogen to dehydrogenation reactions can reduce the rate of coke make. In the present development, it has been found that the combination of the extended cycle with hydrogen introduction results in a surprising stabilization of the production rate in the dehydrogenation process. Although the exact mechanism behind this stabilization of the production rate is not known, it is theorized that the hydrogen introduction has a positive impact on the coke make—either decreasing or at least significantly retarding the coke make. In a preferred embodiment, hydrogen is added at concentrations of up to about 7 mol % $H_2$. But even relatively minor additions of $H_2$, e.g. about 2 mol %, can be effective in reducing the rate of coke make and in stabilizing the production rate for the extended cycle dehydrogenation process.

The hydrogen can be provided through any known source, but because hydrogen is produced in the dehydrogenation reaction, a most effective means of adding hydrogen to the reaction is through a recycle process. In the present development, when the hydrogen recycle process is combined with the extended cycle a stabilization of the production rate in the dehydrogenation process is observed.

The method of the present invention is intended for use in a Houdry-type dehydrogenation process. The method of the present development differs from the methods of the prior art by requiring that the reaction include an extended dehydrogenation cycle and that hydrogen be introduced into the reaction. It is understood that variations may be made to other aspects of the process without exceeding the scope of this development.

What is claimed is:

1. In a standard Houdry process for the dehydrogenation of aliphatic hydrocarbons wherein the process defines a cycle that includes the stages of:
   (a) loading a dehydrogenation catalyst into a reactor to form a catalyst bed wherein the bed defines a top section, a middle section and a bottom section;
   (b) evacuating the catalyst bed;
   (c) reducing the catalyst bed with hydrogen and evacuating the bed;
   (d) introducing an aliphatic hydrocarbon into the catalyst bed as a gas feed at a preselected flow rate and such that the feed initially contacts the top section of the bed and exits after contact with the bottom section and after the hydrocarbon is dehydrogenated;
   (e) steam purging and regenerating the catalyst bed;
   (f) repeating stages (b) through (e); and wherein the length of stages (b) through (e) are controlled by a sequencer, the improvement of
   (1) extending the cycle length by the introduction of a delay of at least one predetermined time interval into at least one stage of the cycle; and
   (2) introducing hydrogen gas, at concentration of up to about 7 mol % $H_2$, into the reaction at stage (d).

2. The process of claim 1 wherein the reaction cycle is extended by the introduction of one or more delays added to a program controlling the sequencer.

3. The process of claim 2 wherein the delay is defined in terms of minutes.

4. The process of claim 2 wherein the delay is defined in terms of seconds.

5. The process of claim 1 wherein the extended reaction cycle produces temperature ranges in each section of the catalyst bed that are greater than the temperature ranges produced in a standard Houdry process.

6. The process of claim 1 wherein the hydrogen gas added at stage (d) is added at concentrations of from about 2 mol % $H_2$ to about 7 mol % $H_2$.

7. The process of claim 1 wherein the hydrogen gas source for introduction at stage (d) is from a recycle process associated with the dehydrogenation reaction.

8. The process of claim 1 wherein a plurality of reactors function in tandem in a manner such that while a first set of reactors is receiving feed (stage d), a second set of reactors is in the regeneration stage (stage e), and wherein the delay introduced in the first set of reactors results in a concomitant delay in the second set of reactors.

9. The process of claim 8 wherein the length of the process stages for each set of reactors is controlled from the sequencer.

10. The process of claim 8 wherein a modification in the length of any process stage in the first set of reactors is accompanied by an essentially equal modification in the length of the same process stage for the second set of reactors.

11. In a standard Houdry process for the dehydrogenation of aliphatic hydrocarbons wherein the process defines a cycle that includes the stages of:
   (a) loading a dehydrogenation catalyst into a reactor to form a catalyst bed wherein the bed defines a top section, a middle section and a bottom section;
   (b) evacuating the catalyst bed;
   (c) reducing the catalyst bed with hydrogen and evacuating the bed;
   (d) introducing an aliphatic hydrocarbon into the catalyst bed as a gas feed at a preselected flow rate and such that the feed initially contacts the top section of the bed and exits after contact with the bottom section and after the hydrocarbon is dehydrogenated;
   (e) steam purging and regenerating the catalyst bed;
   (f) repeating stages (b) through (e); and wherein a plurality of reactors function in tandem in a manner such that while a first set of reactors is receiving feed (stage d), a second set of reactors is in the regeneration stage (stage e), and the length of stages (b) through (e) are controlled by a sequencer, the improvement of
   (1) extending the length of at least one stage of the cycle for each set of reactors by the introduction of one or more delays of a predetermined time interval added to a program controlling the sequencer; and (2) introducing hydrogen gas into the reaction at stage (d) at concentrations of up to about 7 mol % $H_2$.

12. The process of claim 11 wherein the hydrogen gas added at stage (d) is added at concentrations of from about 2 mol % $H_2$ to about 7 mol % $H_2$.

13. The process of claim 11 wherein the hydrogen gas source for introduction at stage (d) is from a recycle process associated with the dehydrogenation reaction.

14. The process of claim 11 wherein the length of the cycle for each set of reactors is controlled from the sequencer.

15. The process of claim 14 wherein the delay introduced in the first set of reactors results in a concomitant delay in the second set of reactors.

\* \* \* \* \*